United States Patent
Chen et al.

[11] Patent Number: 5,917,061
[45] Date of Patent: Jun. 29, 1999

[54] PROCESS FOR PRODUCING CYCLIC ETHERS BY LIQUID PHASE REACTION

[75] Inventors: Shien Chang Chen, Taipei; Cheng Chang Chu; Fu Shen Lin, both of Kaohsiung; June Yen Chou; Ming Hui Chu, both of Kaohsiung, all of Taiwan

[73] Assignee: Dairen Chemical Corporation, Taipei, Taiwan

[21] Appl. No.: 09/067,562

[22] Filed: Apr. 28, 1998

[30] Foreign Application Priority Data

Jan. 15, 1998 [TW] Taiwan ................................. 87100465

[51] Int. Cl.[6] .................................................. C07D 307/08
[52] U.S. Cl. ............................................. 549/509; 549/356
[58] Field of Search ...................................... 549/509, 356

[56] References Cited

U.S. PATENT DOCUMENTS

| 2,251,292 | 8/1941 | Reppe | 260/345 |
| 2,251,835 | 8/1941 | Reppe | 260/345 |
| 4,124,600 | 11/1978 | Jenkins, Jr. | 260/346.11 |
| 4,196,130 | 4/1980 | Huchler et al. | 260/346.11 |
| 4,665,205 | 5/1987 | Yamada et al. | 549/509 |
| 5,099,039 | 3/1992 | Schiraldi et al. | 549/509 |

FOREIGN PATENT DOCUMENTS

| 2509968 | 3/1975 | Germany | C07D 307/00 |
| 2856455 | 12/1978 | Germany | C07D 307/08 |
| 2908759 | 9/1979 | Germany | C03G 13/10 |
| 54-135224 | 10/1979 | Japan | A01N 9/20 |
| 1158562 | 5/1985 | U.S.S.R. | B01J 21/04 |
| 508548 | 7/1939 | United Kingdom . | |

*Primary Examiner*—Ba K. Trinh
*Attorney, Agent, or Firm*—Arnold White & Durkee

[57] ABSTRACT

This invention is directed to a process for producing cyclic ethers by liquid phase reaction, which comprises using a crystalline aluminosilicate zeolite as the catalyst, and subjecting an alkanediol to cyclodehydration at a temperature less than the boiling point of the alkanediol to obtain the corresponding cyclic ether.

7 Claims, No Drawings

PROCESS FOR PRODUCING CYCLIC ETHERS BY LIQUID PHASE REACTION

FIELD OF THE INVENTION

This invention is directed to a process for producing cyclic ethers by liquid phase reaction, which comprises using a crystalline aluminosilicate zeolite as the catalyst, and subjecting an alkanediol to cyclodehydration at a temperature less than the boiling point of the alkanediol to obtain the corresponding cyclic ether.

BACKGROUND OF THE INVENTION

At present, tetrahydrofuran is a widely used cyclic ether. The primary purposes of tetrahydrofuran are as solvent and binder of various resins, as solvent and extraction solvent of printing inks, as the surfactant of synthetic leather and as the material for synthesizing elastic fibers of polytetrahydrofuran. The purpose of other cyclic ethers has not been fully developed yet.

The process of synthesizing cyclic ethers from alkanediols and the catalysts used therein have been well described in the known literatures and patent references. For example, those wherein phosphoric acid is used as a catalyst are disclosed in U.S. Pat. Nos. 2,251,292, 2,251,835 and 4,124,600; those wherein surfuric acid is used as a catalyst are disclosed in Ger. Offen. 2,509,968, U.S. Pat. Nos. 4,665,205 and 5,099,039, Jpn. Tokkyo Koho 78-43,505 and 78-43,506; those wherein aluminum oxide is used as a catalyst are disclosed in U.S. Pat. No. 4,196,130, Brit. 508,548, Ger. Offen. 2,856,455 and USSR SU 1,158,562.

The process of synthesizing cyclic ethers from alkanediols and the catalysts used therein can be classified into two types: one is a process of homogeneous reaction, the other is a process of non-homogeneous reaction. In the process of homogenous reaction, sulfuric acid and phosphoric acid are the representative catalysts. The drawback of such a process is that part of the catalyst is distilled out with the reaction product, resulting in difficulties of separating the catalyst from the reaction product. Moreover, the acidities of sulfuric acid and phosphoric acid catalysts are strong enough to severely corrode the reactor. In addition, when sulfuric acid and phosphoric acid are used as the catalyst, side reactions easily result in which a great amount of coke is produced. The existence of the coke in the reacting liquid may affect the activity of the catalyst. Therefore, in the continuous synthesis process, while the reacting liquid should be removed from the reactor and part of the reacting liquid should be treated, the problem of acidic waste also results. As to the process of non-homogeneous reaction, aluminum oxide is the representative catalyst. The drawback of this process is that the aluminum oxide catalyst is able to exhibit strong activity at high temperatures only, usually at temperatures higher than 250° C. Such high temperatures generally far exceed the boiling points of many alkanediols. Therefore, the reaction must be carried out in a gasous state and the cost of the equipment and operation will be increased to no avail.

The conversion of alkanediols into cyclic ethers using LaHY, CaHY and H-ZSM-6 zeolites was proposed by C. P. Bezouhanova and F. A. Jabur et al. in React. Kinet. Catal. Lett., Vol. 51, No. 1, pp. 177–181 (1993). However, the reaction was carried out in the condition of a gaseous state at temperatures higher than the boiling points of the reactants. The poor selectivity of cyclic ethers is a drawback of this process. It is not satisfactory because the further step of purification is necessary in the subsequent work-up.

In view of these drawbacks of the above-mentioned conventional arts, the inventor has studied intensively and found that they can be resolved by using a crystalline aluminosilicate zeolite as the catalyst which allows the reaction to be carried out in the liquid phase. Therefore, this invention is able to be achieved.

DESCRIPTION OF THE INVENTION

In accordance with the present invention, a process for producing cyclic ethers by liquid phase reaction is provided, which comprises using a crystalline aluminosilicate zeolite as the catalyst, and subjecting an alkanediol to cyclodehydration at a temperature less than the boiling point of the alkanediol to obtain the corresponding cyclic ether.

The process for producing cyclic ethers by liquid phase reaction according to this invention, which comprises using a crystalline aluminosilicate zeolite as the catalyst, is a non-homogeneous process. The acidity of the crystalline aluminosilicate zeolite used in the process according to this invention is stronger than aluminum oxide while its reactivity is stronger too. Therefore, the reaction can be carried out directly in the liquid phase free of pressurized conditions. The life cycle of the catalyst can be extended because of low reaction temperature, little side reaction and the small amount of coke produced.

Moreover, in the process according to this invention, since the reaction is carried out in liquid phase, it is not necessary to greatly increase the reaction temperature and the pressure. Therefore, the high cost of a high temperature heating system and the high cost of equipment resulting from a high pressure operation can be eliminated.

In the process for producing cyclic ethers by liquid phase reaction according to this invention, it is not necessary to carry out the reaction under conditions of high temperature and pressure. This is an advantage not possessed by the conventional non-homogeneous process which utilizes aluminum oxide as a catalyst. No matter whether fixed bed or continuous stirrer is used in the process according to this invention, since the catalyst will not be distilled out with the reaction resultant, neither the difficulties of separating the catalyst from the reaction resultant, nor the acidic waste problem, which exist in the homogeneous process, exist in this invention. This is an advantage not possessed by the conventional homogeneous process which utilizes sulfuric acid as a catalyst.

The alkanediols employed in the process of this invention are $C_{3-8}$-alkanediols having two hydroxy groups in each molecule, such as 1,4-butanediol, 1,5-petanediol, 1,4-petanediol, 1,6-hexanediol, etc.

The crystalline aluminosilicate zeolite catalysts employed in the process of this invention are those wherein the molar ratio of silica to aluminum oxide is 30~500:1 and the constraint index is 1~12, for example, ZSM-5, ZSM-11, ZSM-12, ZSM-22, ZSM-34, ZSM-35, ZSM-48 etc.

The amount of the catalyst employed is 0.001 to 100 times, preferably 0.01 to 10 times, the weight of alkanediols.

The reaction temperature employed in the process of this invention depends on the kinds of starting material. The reaction is generally carried out at a temperature in the range of 90° C. to the boiling point of the starting material. If the reaction temperature is lower than 90° C., the reaction rate is low; if the reaction temperature is higher than the boiling point of the starting material, by-products of the reaction may increase.

The reaction pressure is generally in the range of 0.1 to 10 atms, preferably in the range of 1 to 5 atms.

The reactor for carrying out the process of this invention can be subjected to batch-type or continuous-type reaction, with or without stirring, depending on the condition.

The process of this invention is exemplified by the following examples, but the scope of this invention is by no means limited. Various changes and modifications may be made to this invention without departing from the spirit and the scope of this invention.

In these following examples, the analysis of the products is performed and quantified by gas chromatography (GC).

EXAMPLE 1

In a continuous-type stirring reactor equipped with stirring apparatus, temperature controlling apparatus and cooling apparatus, the reactant, 200 g of 1,4-butanediol, and 5 g of ZSM-5 catalyst were added. While the reaction was performed at a controlled temperature of 180° C., tetrahydrofuran product and water were distilled out. After cooling, the product was obtained. Forty grams of tetrahydrofuran product was obtained in one hour of reacting duration.

EXAMPLES 2~7

In the same reactor as in Example 1, 200 g of 1,4-butanediol reactant was added, then 10 g of various catalysts as shown in Table 1 below were added, respectively. The reaction was carried out at a controlled temperature of 180° C. for 2 hours to obtain tetrahydrofuran product. The result is shown in Table 1.

TABLE 1

| Example | Catalyst | Weight of Tetrahydrofuran (g) |
|---|---|---|
| Example 2 | ZSM-11 | 37 |
| Example 3 | ZSM-12 | 35 |
| Example 4 | ZSM-22 | 29 |
| Example 5 | ZSM-34 | 31 |
| Example 6 | ZSM-35 | 29 |
| Example 7 | ZSM-48 | 27 |

EXAMPLES 8~11

A fixed bed reactor with 12 mm of outer diameter and 80 cm of length, equipped with temperature controlling apparatus and feed stream controlled apparatus, was used as the reactor set. Thirty milliliters of ZSH-5 catalyst was added. Then, the alkanediol reactant was continuously fed in at a flow rate of 20 grams per hour through the controlling apparatus. One hour later, the corresponding cyclic ether product was obtained. The result is shown in Table 2.

TABLE 2

| Example | Alkanediol | Reaction Temperature (° C.) | Cyclic Ether (g) |
|---|---|---|---|
| Example 8 | 1,4-Butanediol | 150 | Tetrahydrofuran(15.8) |
| Example 9 | 1,5-Pentanediol | 160 | Tetrahydropyran(15.1) |
| Example 10 | 1,4-Pentanediol | 140 | 2-Methyltetrahydrofuran(13.6) |
| Example 11 | 1,6-Hexanediol | 170 | Perhydrooxepine(14.4) |

EXAMPLE 12

In the same reactor as in Example 1, 300 g of 1,4-butanediol reactant and 30 g of water were added, then 30 g of ZSM-22 catalyst was also added. The reaction was carried out at a controlled temperature of 150° C. for 3 hours to obtain 120 g of tetrahydrofuran product.

EXAMPLE 13

In the same reactor as in Example 1, 200 g of 1,4-butanediol reactant and 20 g of ZSM-35 catalyst were first added, then 1,4-butanediol was continuously added at a flow rate of 100 grams per hour. The reaction was carried out at a controlled temperature of 180° C. for 2 hours to obtain 150 g of tetrahydrofuran product.

EXAMPLE 14

In the same reactor as in Example 8~11, 40 ml of ZSM-22 catalyst was added in the fixed bed reactor, then 1,5-pentanediol reactant was continuously fed in at a flow rate of 20 grams per hour through the controlling apparatus. One hour later, 15.3 g of tetrahydrofuran was obtained.

COMPARATIVE EXAMPLE 1

In the same reactor as in Example 8~11, 30 ml of ZSM-5 catalyst was added in the fixed bed reactor, then 1,4-butanediol reactant was continuously fed in at a flow rate of 20 grams per hour through the controlling apparatus. One hour later, tetrahydrofuran product was obtained. The result and the comparison with the Examples are shown in Table 3.

TABLE 3

| Example | Alkanediol | Catalyst | Reaction Temperature (° C.) | Selectivity of Cyclic Ether (Molar Percent) |
|---|---|---|---|---|
| Example 8 | 1,4-Butanediol | ZSM-5 | 150 | 99 |
| Comparative Example 1 | 1,4-Butanediol | ZSM-5 | 250 | 95 |

COMPARATIVE EXAMPLE 2

In the same reactor as in Example 8~11, 40 ml of ZSM-22 catalyst was added in the fixed bed reactor, then 1,5-pentanediol reactant was continuously fed in at a flow rate of 20 grams per hour through the controlling apparatus. One hour later, tetrahydrofuran product was obtained. The result and the comparison with the Examples are shown in Table 4.

TABLE 4

| Example | Alkanediol | Catalyst | Reaction Temperature (° C.) | Selectivity of Cyclic Ether (Molar Percent) |
|---|---|---|---|---|
| Example 14 | 1,5-Pentanediol | ZSM-22 | 170 | 99 |
| Comparative Example 2 | 1,5-Pentanediol | ZSM-22 | 270 | 92 |

COMPARATIVE EXAMPLE 3

In the same reactor as in Example 1, 300 g of 1,4-pentanediol reactant and 30 g of water were added while 15 g of catalysts ZSM-11, γ-type zeolite and mordenite were added respectively to carry out the reactions. While the reactions were performed, cyclic ether products and water were distilled out. After cooling, the products were obtained. The reactions were carried out for 1 hour. The result is shown in Table 5.

TABLE 5

| Comparative Example | Alkanediol | Reaction Temperature (° C.) | Catalyst | 2-Methyltetra-hydrofuran |
|---|---|---|---|---|
| Comparative Example 3 | 1,4-Pentanediol | 165 | ZSM-11 | 158 |
| | | | Y-type Zeolite | 64 |
| | | | Mordenite | 37 |

It is known from the results of the above Examples 1~14 and Comparative Examples 1 and 2 that, when the reaction temperature is lower than the boiling point of the reactant (i.e., when the reaction is carried out in liquid phase), high selectivity of cyclic ether is obtained (i.e., there is no by-product formed). It is seen from Comparative Example 3 that a better yield of cyclic ether is obtained when crystalline aluminosilicate zeolite is used as the catalyst in the present invention.

What is claimed is:

1. A process for producing cyclic ethers by liquid phase reaction, which comprises using a crystalline aluminosilicate zeolite as the catalyst, and subjecting an alkanediol to cyclodehydration at a temperature from 90° C. to less than the boiling point of the alkanediol to obtain the corresponding cyclic ether; wherein the molar ratio of silica to aluminum oxide in the crystalline aluminosilicate zeolite catalyst is 30~500:1 and the constraint index is 1~12.

2. The process according to claim 1, wherein the alkanediol is a $C_{3-8}$-alkanediol having two hydroxy groups in each molecule.

3. The process according to claim 1, wherein the reaction temperature is from 120° C. to 200° C.

4. The process according to claim 1, wherein the reaction is carried out at a pressure of from 0.1 to 10 atms.

5. The process according to claim 1, wherein the amount of the catalyst is 0.001 to 100 times the weight of the alkanediol.

6. The process according to claim 5, wherein the amount of the catalyst is 0.01 to 10 times the weight of the alkanediol.

7. The process according to claim 1, wherein cyclodehydration is carried out in batch-type, fixed-bed, continuous-type, with or without stirring.

* * * * *